United States Patent
De Vlaminck et al.

(10) Patent No.: US 8,027,040 B2
(45) Date of Patent: Sep. 27, 2011

(54) METHOD FOR DETERMINING AN ANALYTE IN A SAMPLE

(75) Inventors: Iwijn De Vlaminck, Nederland (BE); Pol Van Dorpe, Spalbeek (BE); Liesbet Lagae, Herent (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 446 days.

(21) Appl. No.: 12/220,346

(22) Filed: Jul. 24, 2008

(65) Prior Publication Data
US 2009/0027681 A1 Jan. 29, 2009

Related U.S. Application Data

(60) Provisional application No. 60/951,484, filed on Jul. 24, 2007.

(51) Int. Cl.
*G01N 21/55* (2006.01)
(52) U.S. Cl. ...................................... 356/445
(58) Field of Classification Search .................. 356/441, 356/445–448, 432, 301; 385/12, 17, 30; 372/45.01–46.016, 26, 28, 96, 38.01–38.02, 372/32; 422/82.05, 82.11
See application file for complete search history.

(56) References Cited

U.S. PATENT DOCUMENTS

| | | | |
|---|---|---|---|
| 5,815,278 A * | 9/1998 | Johnston et al. | 356/445 |
| 2003/0215865 A1* | 11/2003 | Mayer et al. | 435/6 |
| 2005/0063870 A1* | 3/2005 | Fukushima et al. | 422/82.05 |
| 2006/0034729 A1* | 2/2006 | Poponin | 422/82.05 |
| 2006/0274315 A1* | 12/2006 | Saito | 356/445 |
| 2007/0194357 A1* | 8/2007 | Oohashi et al. | 257/292 |
| 2007/0211985 A1* | 9/2007 | Duer | 385/12 |

OTHER PUBLICATIONS

Iwijn De Vlaminck, Local Electrical Detection of Single Nanoparitcle Plasmon Resonance, Feb. 22, 2007, Nano Letters, vol. 7, No. 3, pp. 703-706.*
Haes, A. J. et al., "A unified view of propagating and localized surface plasmon resonance biosensors", Analytical and Bioanalytical Chemistry, 2004, 379(7-8), 920-930.
Frederix, F. et al., "Biosensing based on light absorption of nanoscaled gold and silver particles", Analytical Chemistry, 2003, 75(24), 6894-6900.
Yu, Z. et al., "Design of midinfrared photodetectors enhanced by surface plasmons on grating structures", Applied Physics Letters, 2006, vol. 89, 151116.

(Continued)

*Primary Examiner* — Tarifur Chowdhury
*Assistant Examiner* — Michael P Lapage
(74) *Attorney, Agent, or Firm* — McDonnell Boehnen Hulbert & Berghoff LLP

(57) ABSTRACT

In one aspect of the invention, a method or apparatus is described for determining concentration(s) of one or more analytes in a sample using plasmonic excitations. In another aspect, a method relates to designing systems for such concentration determination, wherein metallic nanostructures are used in combination with local electrical detection of such plasmon resonances via a semiconducting photodetector. In certain aspects, the method exploits the coupling of said metallic nanostructure(s) to a semiconducting photodetector, said detector being placed in the "metallic structure's" near field. Surface plasmon excitation can be transduced efficiently into an electrical signal through absorption of light that is evanescently coupled or scattered in a semiconductor volume. This local detection technique allows the construction of sensitive nanoscale bioprobes and arrays thereof.

21 Claims, 3 Drawing Sheets
(3 of 3 Drawing Sheet(s) Filed in Color)

OTHER PUBLICATIONS

Rand, B. P. et al., "Long-range absorption enhancement in organic tandem thin-film solar cells containing silver nanoclusters", Journal of Applied Physics, 2004, 96(12), 7519-7526.

De Vlaminck, I. et al., "Local electrical detection of single nanoparticle plasmon resonance", Nano Letters, 2007, 7(3), 703.

Mapel, J. K. et al., "Plasmonic excitation of organic double heterostructure solar cells", Applied Physics Letters, 2007, vol. 90, 121102.

Collin, S. et al., "Resonant-cavity-enhanced subwavelength metal-semiconductor-metal photodetector", Applied Physics Letters, 2003, 83(8), 1521-1523.

Schaadt, D. M. et al., "Enhanced semiconductor optical absorption via surface plasmon excitation in metal nanoparticles", Applied Physics Letters, 2005, vol. 86, 063106.

* cited by examiner

METHOD FOR DETERMINING AN ANALYTE IN A SAMPLE

CROSS-REFERENCE TO RELATED APPLICATIONS

The present application claims priority under 35 §U.S.C. 119(e) to U.S. Provisional Patent Application Ser. No. 60/951,484, filed Jul. 24, 2007, which is hereby incorporated herein by reference in its entirety.

BACKGROUND OF THE INVENTION

1. Field of the Invention

The invention relates generally to methods and apparati for determining concentration(s) of one or more analytes in a sample using plasmonic excitations and apparati and methods for designing systems for such concentration determination.

2. Technical Background

Surface Plasmon Polaritons (SPP) are electromagnetic excitations at the surface of metals and in metal nanoparticles.

A number of recent reports [1-6] show that surface plasmon excitations in metal particles or metal films can cause an enhancement of the light absorption efficiency of organic [2,4] and inorganic photodetectors [1, 3, 5-6].

In biosensing, the importance of plasmonics relies in high optical energy confinement and strong local enhancement of electric fields. Biorecognition is achieved in (localized) surface plasmon resonance ((L)SPR) biosensors [Haes, A. J.; Van Duyne, R. P. *Anal. Bioanal. Chem.* 2004, 379, 920; Frederix, F. et al. s, G. *Anal. Chem.* 2003, 75, 6894] through the detection of (L)SPR spectral changes caused by adsorbate-induced changes in local dielectric constant. In a very common configuration, the SPR spectrum of a nanoparticle surface or nanostructured surface is studied with an optical detector in the far field at large distance from the metal particle or film [7].

REFERENCES

[1] Z. Yu, G. Veronis, S. Fan and M. L. Brongersma, Appl. Phys. Lett. 89, 151116 (2006).
[2] B. P. Rand, P. Peumans and S. R. Forrest, J. Appl. Phys. 96, 7519, (2004).
[3] I. De Vlaminck, P. Van Dorpe, L. Lagae and G. Borghs, Nano Letters, 7, 703 (2007).
[4] J. K. Mapel, M. Singh, M. A. Baldom and Celebi, Appl. Phys. Lett. 90, 121102 (2007).
[5] S. Collin, F. Pardo, and J.-L. Pelouard, Appl. Phys. Lett. 83, Issue 8, 1521 (2003).
[6] D. M. Schaadt B. Feng, and E. T. Yub, Appl. Phys. Lett. 86, 063106 (2005)
[7] F. Frederix, J.-M. Friedt, K.-H. Choi, W. Laureyn, A. Campitelli, D. Mondelaers, G. Maes and G. Borghs Anal. Chem. 75, 6894 (2003).

SUMMARY OF THE INVENTION

A method or apparatus according to one embodiment of the present invention relates to determining concentration(s) of one or more analytes in a sample using plasmonic excitations. A method or apparatus according to another embodiment of the present invention relates to designing systems for such concentration determination, wherein metallic nanostructures are used in combination with local electrical detection of such plasmon resonances via a semiconducting photodetector.

In one aspect of the invention, the method exploits the coupling of said metallic nanostructure(s) to a semiconducting photodetector, said detector being placed in the "metallic structure's" near field. Surface plasmon excitation can be transduced efficiently into an electrical signal through absorption of light that is evanescently coupled or scattered in a semiconductor volume. This local detection technique allows the construction of sensitive nanoscale bioprobes and arrays thereof.

One aspect of the invention is based on the insight that the strong dependence of the surface plasmon properties on the optical properties of their surroundings makes them ideal for local sensing applications, such as (bio)chemical and environmental sensing. In particular, an advantage can be obtained in combination with the local enhancement of the electromagnetic field to increase or influence the light absorption efficiency in photodetectors. This can result in an absorption spectrum that depends on the properties of the plasmonic excitation, if these effects and their coupling are properly exploited in the design.

Integration of the particle or film on a local photodetector allows the transduction of the plasmon excitation locally to an electrical signal. Such a local transduction technique offers a number of advantages. First of all, the ability to detect the plasmon resonance of individual structures leads to enhanced system-sensitivity and lowered detection limits in biosensing. Furthermore, the local transduction of optical signals to the electrical domain provides possibilities for large-scale integration, multiplexed detection and/or miniaturization.

In one embodiment of the invention, a specific geometry of a plasmon-enhanced photodetector device is presented. In this geometry, the metal film completely covers the photodetector. This has two major advantages. First of all, the metal film or particle can be optically coupled to a photodetector volume to enhance the photodetector signal and to make the device (bio)chemically specific. Secondly, the metal film serves as a passivation of the photodetector volume. By completely covering the device, the resulting biosensing device is made more stable; chemical degradation of the semiconductor is avoided and the metal film effectively screens the photodetector from unwanted influences of external charges.

Accordingly, one embodiment of the present invention is a method for determining the concentration of an analyte using a substrate comprising a conductive region and a recognition layer, the conductive region having a first surface operatively coupled with the recognition layer, the conductive region comprising at least one metal particle or structure (e.g. Au or Ag) and a semiconductor; the method comprising:
  contacting the substrate with the analyte to bind at least a portion of the analyte with the recognition layer;
  directing (e.g. via air, liquid or a waveguide) radiation (e.g. having a wavelength in the UV, visible or infrared part of the spectrum) to the conductive region and the recognition layer, the combination of the at least one metal particle or structure, the semiconductor and the analyte exhibiting plasmon effects when the radiation is directed to the conductive region and the recognition layer; and
  electrically transducing the response of the a plasmonic excitation of the combination of the metal particle or structure, analyte and semiconductor volume, through light absorption in the semiconductor (e.g. preferably placed locally to said metal particle or structure) and subsequent change of the conductivity of said semiconductor (e.g. acting as a photodetector).

At least part of the spectrum related to said plasmon effect can be absorbed in the semiconductor through scattering into the semiconductor and subsequent absorption or through evanescent coupling to the semiconductor.

The method can also include determining the concentration of the analyte from at least part of the spectrum of said light absorption (e.g. by determining a change of at least part of the spectrum of said light absorption and determining said concentration from said change).

In certain embodiments of the invention, the method may include the following optional features:

The photodetector can be placed within the near field of the plasmonic excitation at the surface of said metal particle or structure.

The photodetector and said metal particle (e.g. the shape) are preferably designed to optimize transduction from radiation to electrical signal within said photodetector.

The photodetector and said metal particle or structure (e.g. the shape) are optionally designed to optimize the sensitivity of said absorption spectrum to binding of said analytes.

The photodetector can be a free-standing structure.

The shape of said particle and/or said photodetector can be rectangular.

The photodetector can be made from one or more light absorbing semiconductor materials (e.g. GaAs and AlGaAs; Si; SiGe; organic semiconductors).

The one or more semiconductor materials can form a photosensitive diode or a photoconductor, or a structure displaying a photoelectric response.

The metal particles may form a film covering or encapsulating partly or completely said photodetector.

The encapsulating metal film or structure preferably acts as a protection layer for the photodetector from the (e.g. liquid) environment.

The method may include that said absorption spectrum is compared with a reference spectrum.

The encapsulating metal film or structure may act as an electronic shielding layer, screening the influence of electronic charges in the environment, e.g. in a liquid, on the electronic properties of the semiconductor volume.

The radiation may be directed from free space or from a light or plasmon waveguide.

In the method according to one embodiment of the invention, the analyte can be bound to at least one nanoparticle, said nanoparticles contributing to the plasmon effect after binding of the analyte with the recognition layer (i.e. also called a sandwich assay).

In the method according to one embodiment of the invention, a molecular resonance of the analyte can change said absorption spectrum.

In the method according to one embodiment of the invention, said binding between analyte and recognition layer is the surface interaction between a gas analyte and a solid recognition layer.

In another embodiment of the invention, the present invention provides a method for parallel determination of the concentration of a plurality of analytes within a sample, the method comprising substantially simultaneously performing any of the above methods on a plurality of places on said substrate, each of said places having at least one metal particle and a specific recognition layer of one of said plurality of analytes with a plurality of photodetectors. At each of said places said photodetector and said metal particle (e.g. the shape) can be designed or adapted to optimize the transduction from radiation to electrical signal within said photodetector for the metal particle, photodetector and recognition layer combination at a specific place. In the method N metal particles or structures can be constructed local to M semiconductor volumes.

The mechanical properties of the freestanding structure may also be measured to provide additional information on the analyte.

In one embodiment of the invention, the substrate is part of a microfluidic system.

The present invention also provides a method for designing a system for determining a concentration of an analyte within a sample, said system comprising a substrate, said substrate comprising a conductive region and a recognition layer, the conductive region having a first surface operatively coupled with the recognition layer, the conductive region comprising at least one metal particle (e.g. Au) and a semiconductor, said system further comprising a semiconducting photodetector placed local to said metal particle, the method comprising:

inputting material characteristics of said metal particle and said semiconductor;

inputting characteristics of said analyte;

inputting radiation characteristics;

creating a model, exploiting said material, analyte and radiation characteristics, said model describing the plasmon effects exhibited by said at least one particle and said analyte when radiation is directed through the conductive region and the recognition layer, said model further describing the light absorption by said semiconductor, in particular the enhancement thereof by the presence of said particle(s); and determining design parameters (e.g. distance between said photodetector and said particle, shape of said particle, shape of said photodetector, radiation field distribution) by performing simulation experiments with said model.

The model may be, for example, a Finite Difference Time Domain model.

The design parameter determination may be, for example, at least targeted for maximized sensitivity.

Another embodiment of the present invention is a structure for determining the concentration of an analyte, the structure comprising a substrate;

a conductive region, said conductive region comprising at least one metal particle or structure (e.g. Au or Ag);

a semiconductor region in direct contact with said conductive region or local to said conductive region or in the near-field of said conductive region;

a recognition layer operatively coupled with a first surface of said the conductive region; and an analyte in contact with said recognition layer.

In the structure said recognition layer can be chosen such that it binds at least a portion of said analyte.

The combination of the at least one metal particle or structure, the semiconductor and the analyte can exhibit plasmon effects upon directing (e.g. via air, liquid or a waveguide) radiation (e.g. having a wavelength in the UV, visible or infrared part of the spectrum) to the conductive region and the recognition layer.

In the structure said semiconductor can be chosen such that the response of the said plasmonic excitation of the combination of the metal particle or structure, analyte and semiconductor volume, is electrically transduced through light absorption in the semiconductor and subsequent change of the conductivity of said semiconductor (e.g. or i.e. when acting as a photodetector).

At least part of the spectrum related to said plasmon effect can be absorbed in the semiconductor through scattering into the semiconductor and subsequent absorption or through evanescent coupling to the semiconductor.

The concentration of the analyte may be, for example, determined from at least part of the spectrum of said light absorption (e.g. by determining a change of at least part of the spectrum of said light absorption and determining said concentration from said change).

The structure may be, for example, included in a disposable test cartridge.

The structure may be, for example, part of a microfluidic system.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
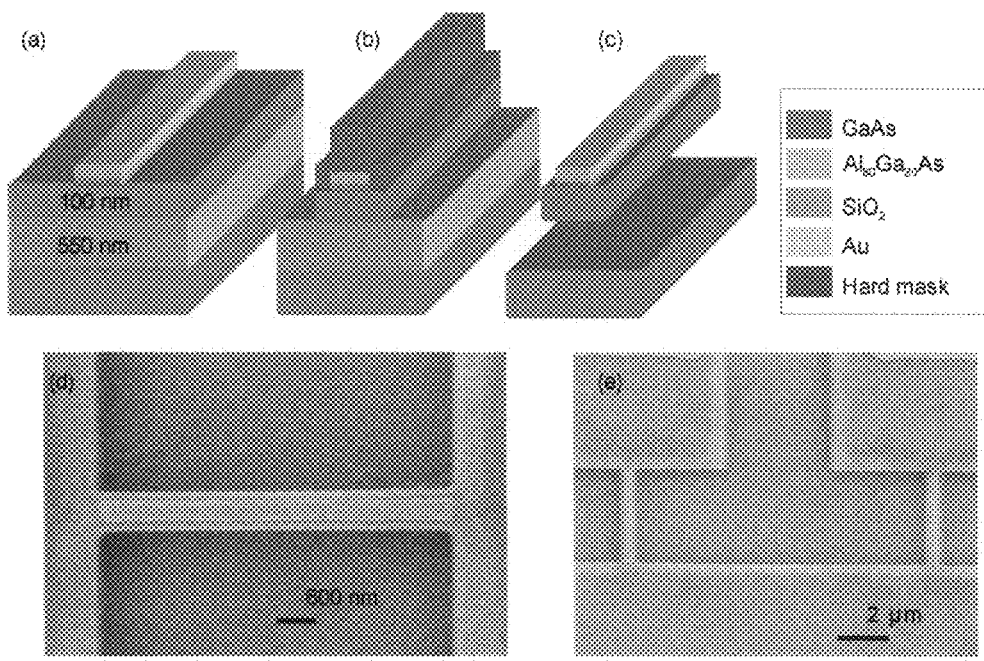
FIG. 1: (a)-(d) shows a fabrication sequence for the gold structure coupled to a semi-conducting photodetector. (a) EBL and lift-off for definition Au—SiO$_2$ structure. (b) Second e-beam EBL, definition hard mask, dry etch of GaAs. (c) HF-based selective etch of Al$_{80}$Ga$_{20}$As, resulting in a freestanding GaAs detector. (d) Scanning electron micrographs of a fabricated structure, width GaAs detector 600 nm, Au-structure dimensions: 0.3×5×0.03 μm. In panel (e) the detectors with and without particle are shown.

One aspect of the present invention is a method, suitable for biosensing applications, in which plasmonic excitations (typically resonant excitations) in metals are detected or transduced electrically, and in which detection is performed locally, hence enabling excitations of even a single metal nanoparticle. Any reference to the term nanoparticle in the following should be construed broadly to include any suitable nanostructure, e.g. as a film.

Sub-wavelength sized noble metal particles show a pronounced plasmon induced resonance in their scattering and absorption spectrum for light in the visible and NIR range. The polarizability of the nanoparticle and therefore its plasmon resonance are strongly dependent on the dielectric properties of the particle's immediate environment. This property allows for the detection of biomolecular binding events at the surface.

In one aspect, the present invention provides a technique for the transduction of the plasmon excitation, which is, for example, capable of detecting resonance of a nanostructured metal film and even in a single metal nanoparticle into an electrical signal. Such a technique allows the development of very sensitive biomolecular probes for which large parallelism can be exploited.

In certain embodiments of the invention, the transduction occurs in a coupled metal-semiconductor hybrid structure, where the plasmon excitation occurs in the metal nanostructure or particle, while the semiconductor transduces light into an electronic signal. When this hybrid structure is illuminated by light, the plasmonic excitations in the metal nanostructure or particle cause both evanescent coupling and scattering of light into the semiconductor cavity of the photodetector, providing efficient transduction. The spectrum of the photosensitive semiconductor shows pronounced effects (such as resonance features) related to the plasmonic excitations. For example, depending on the dimensions, dipolar or multipolar resonances can be recorded.

In one aspect of the invention, a method is provided to perform (bio)chemical sensing through tracking the absorption spectrum and measuring analyte-absorption induced changes of this spectrum. The changes in the absorption spectrum can be compared with a reference spectrum. The reference spectrum can be provided by a reference detector constructed locally or non-locally. The reference spectrum can also be a previously recorded spectrum. The reference spectrum can also be a spectrum recorded for an excitation with light with a different polarization.

In certain embodiments of the invention, a recognition layer can be provided on the metal-semiconductor hybrid system to allow for specific detection of specific (bio)chemical analytes. The analyte may be a biomolecule that can bind to another molecule in the recognition layer by an affinity-based biochemical reaction. The analyte may bind to the recognition layer in a direct assay, where the analyte changes the dielectric constant and the plasmonic excitation and thus the absorption spectrum. The analyte may change the plasmonic excitation indirectly, e.g. by overlapping with its own molecular resonance absorption bands (e.g., FT-IR, SERS). The analyte may bind to another nanoparticle and to the recognition layer in a sandwich assay such that the nanoparticle contributes to the changes in absorption spectrum. The nanoparticle may be, for example, a metallic nanoparticle, a semiconducting nanoparticle or a hybrid nanoparticle that can change the plasmonic excitation via a change in the optical properties (dielectric constant, but also e.g. fluorescence). The analyte may also be a gas which is absorbed by the recognition layer e.g. a thin organic layer or adsorbed.

In one embodiment of the invention, the light scattered and/or evanescently coupled by a nanoparticle is collected and sensed by means of a sensitive photoconductor such as a GaAs photoconductor in the particle's near-field. Other photoelectric devices such as semiconducting pn junctions, pin junctions or Shottky diodes, can also be exploited or used.

In certain embodiments of the invention, the optical index contrast between the semiconductor and the environment is large, in order to provide more efficient transduction. This can be realized by e.g. utilizing thin semiconducting layers on top of a substrate with a low dielectric constant (such as e.g. Si on insulator). However, the invention can be practiced using a smaller optical index contrast between the semiconductor and the environment.

In a specific embodiment of the invention, a freestanding photoconductor can be fabricated with a nanoparticle such as an Au nanoparticle on top by means of top-down fabrication methods in the semiconductor material system such as a GaAs—AlGaAs material system. The nanoparticle can be in the shape of a rectangular film. This approach allows tailoring the shape of the gold nanoparticle and detector structures to specific needs. Making the photoconductor freestanding not only increases the efficiency of light coupling of the radiating particle to the photoconductor but also reduces contributions of leak currents and light absorption in the substrate to the measured response.

Additionally this approach opens up the possibility of separately measuring the mass of the biomolecules through the measurement of changes in the mechanical resonance frequency of the photoconductor. The response of the nanoparticle-photoconductor system versus wavelength of the light can, for instance, be measured in a balanced method with a reference photoconductor without a nanoparticle. Furthermore, the detection of the mechanical resonance frequency of the freestanding structures can be performed using an interferometric technique.

In another embodiment of the invention, a freestanding photoconductor can be fabricated with a Au film on top of a GaAs—AlGaAs material system.

Layered structures for the optical detector can be deposited by means of Molecular Beam Epitaxy, sputtering CVD, PECVD or any other deposition technique known in the art on top of insulating or semi-insulating substrates, for example a GaAs semi-insulating substrate. One or more sacrificial layers for example $Al_{80}Ga_{20}As$ layer (thickness between 100 nm and 1000 nm), can be grown followed by the deposition of at least an active layer, for example n-GaAs ($2e^{18}$ $cm^{-3}$), (thickness between 20 nm and 500 nm). If needed, patterning of the layers can be done by lithography and dry and/or wet etching. Also Electron beam lithography (EBL) can be used to define a pattern in a resist layer (for example PMMA-PMMA/MA.) An insulating layer, for example $SiO_2$ layer (thickness between 2 nm and 50 nm) can be deposited for example by sputtering. On top a conducting, for example Au, layer (e.g. having a thickness between 10 nm and 100 nm) can be deposited and patterned. Patterning or transferring the layer structure can be done with lift-off or lithography followed by dry and/or wet etching.

Patterning of the underlying insulating or semi-insulating substrate (for example GaAs) can be done by any method known in the art, for example lithography followed by dry and/or wet etching or by using a hard mask (for example Ge/Ti 50 nm/50 nm) made by for example deposition and lift-off. The hard mask pattern is than transferred in the underlying insulating or semi-insulating substrate (for example GaAs) for example through reactive ion etching, using for example a Cl—Ar plasma. Underetching of the devices, for example HF-based (selective $Al_{80}Ga_{20}As$ etch) and rinsing with $H_2O$, acetone and isopropyl alcohol, the hard mask can be removed.

In a last step, Ohmic contacts (for example AuGe/Ni/Au, 120 nm/15 nm/60 nm) can be defined for example with optical lithography evaporation and lift-off. It is also possible to deposit the conducting layers for the contacts followed by lithography and dry and/or wet etching.

The method, the underlying physical mechanism and the design approach are further described in more detail below.

Surface Plasmons are electromagnetic oscillations mediated by charge oscillations. They occur at the surface of noble metals and in noble metal nanoparticles with resonance frequencies in the visible and IR spectrum. The properties of Surface Plasmons have received great interest in recent years as it is recognized that they have the ability to overcome the size-mismatch between diffraction limited optical components and nanoscale objects, opening up new possibilities in, e.g. optical signal processing and biosensing. It has been shown that Surface Plasmon mediated electromagnetic waveguiding is feasible in sub-wavelength metallic wires or chains of metal nanoparticles. Furthermore efficient modal coupling between Plasmon waveguides and dielectric waveguides has been demonstrated.

In biosensing, the importance of plasmonics relies in high optical energy confinement and strong local enhancement of electric fields. Biorecognition is achieved in (e.g. localized) surface plasmon resonance ((L)SPR) biosensors through the detection of (L)SPR spectral changes caused by adsorbate-induced changes in local dielectric constant. In a very common configuration, the SPR spectrum of a film or nanostructured surface is studied with an optical detector in the far field at large distance from the metal particle or film.

The ability of detecting the Plasmon resonance of individual structures leads to enhanced system-sensitivity and lowered detection limits in biosensing. Local electrical signal transduction has the added advantage that it offers the possibility of constructing bioassays that exploit large-scale parallelism and multiplexing, allowing more information to be extracted from one sample at a time. Furthermore the construction of fully integrated bio-probes becomes possible with such technique.

The current invention may also aid in the development of components for optical to electrical signal transduction, useful in optical circuitry.

In the example implementation below, the optical detector is a semiconducting photoresistor, the particle is fabricated directly on top of the detector. The particle may be in the form of a film. A reference detector with identical dimensions but without metal particle is constructed nearby (at a distance of 12.5 microns). Through comparison of the response of the reference detector and particle-enhanced detector, particle related spectral features can be discerned from features related to the wavelength specificity of the photodetector and wavelength-dependent properties of the various components in the measurement setup. An oxide layer between the particle and semiconductor serves as electrical isolation but also allows tuning of the optical response. The photodetectors can be made freestanding: as a result parasitic current paths can be avoided, the optical response can be tuned and, particle-to-detector light coupling can be enhanced due to an increase in optical index contrast.

In an example implementation, layer structures for the optical detector are defined by means of Molecular Beam Epitaxy on GaAs semi-insulating substrates. The active layer, 100 nm n-GaAs ($2e^{18}$ $cm^{-3}$), is grown on a 560 nm sacrificial $Al_{80}Ga_{20}As$ layer. In FIG. 1 (a)-(c) the fabrication scheme for the gold structure coupled to a semi-conducting photodetector is outlined. Electron beam lithography (EBL) was used to define a pattern in a PMMA-PMMA/MA resist layer. A 10 nm $SiO_2$ layer is deposited by sputtering; subsequently a 30 nm layer of Au is evaporated and the layer structure is transferred with lift-off. After a second EBL step, a hard mask (Ge/Ti 50 nm/50 nm) is made by means of evaporation and lift-off. The pattern is then transferred in the GaAs layer through reactive ion etching in a Cl—Ar plasma. After the subsequent, HF-based, underetching of the devices (selective $Al_{80}Ga_{20}As$ etch) and rinsing with $H_2O$, acetone and isopropyl alcohol, the hard mask is removed. In the last step ohmic contacts (AuGe/Ni/Au, 120 nm/15 nm/60 nm) were defined with optical lithography evaporation and lift-off. In FIG. 1 (d)-(e) a scanning electron micrograph (SEM) image of a finished device is shown. Panel (e) shows the detector with particle and the reference detector without such a particle.

The semiconductor cavity on which the metal structure is fabricated significantly influences the structure's response. The polarizability of the substrate gives rise to anisotropic behavior, and significant changes in resonance frequency and bandwidth. The influence of the substrate is usually modeled by considering electromagnetic coupling with the image charges induced in the substrate. The substrate induced inhomogeneity of the local electric field gives rise to efficient coupling of the applied fields to multipole responses of the metal structure. The non-spherical nature of the metal structure makes it particularly susceptible to multipolar excitations. Nanostructuring of the dielectric leads to waveguide and cavity effects. The coupling of dipole scatterers to waveguide modes has been calculated and it was shown that highly efficient coupling can be achieved in case of a high index contrast of the waveguide system. Furthermore, the semiconductor provides additional channels for energy dissipation, broadening the Plasmon response.

In order to study the optical response of the particle-semiconductor cavity system subject to an incident electromagnetic wave, we employ a two-dimensional Finite Difference Time-Domain (FDTD) method (see, e.g., www.lumerical.com/fdtd). Experimental data on the frequency dependent dielectric constants of Au, $SiO_2$ and GaAs, including real and imaginary parts were fitted and used in the model. The frequency-dependent absorption in the GaAs detector layer was extracted by monitoring the optical power flowing in and out of the semiconductor volume. Results for a model of a semiconductor structure with a particle attached to it are compared to results for a model of an identical semiconductor structure without particle. The simulation area was 1.5 $\mu m \times 1.2$ $\mu m$ large with Perfectly Matched Layer (PML) type boundaries. After a convergence analysis, a grid size of 2 nm×2 nm was chosen.

Figure 2:
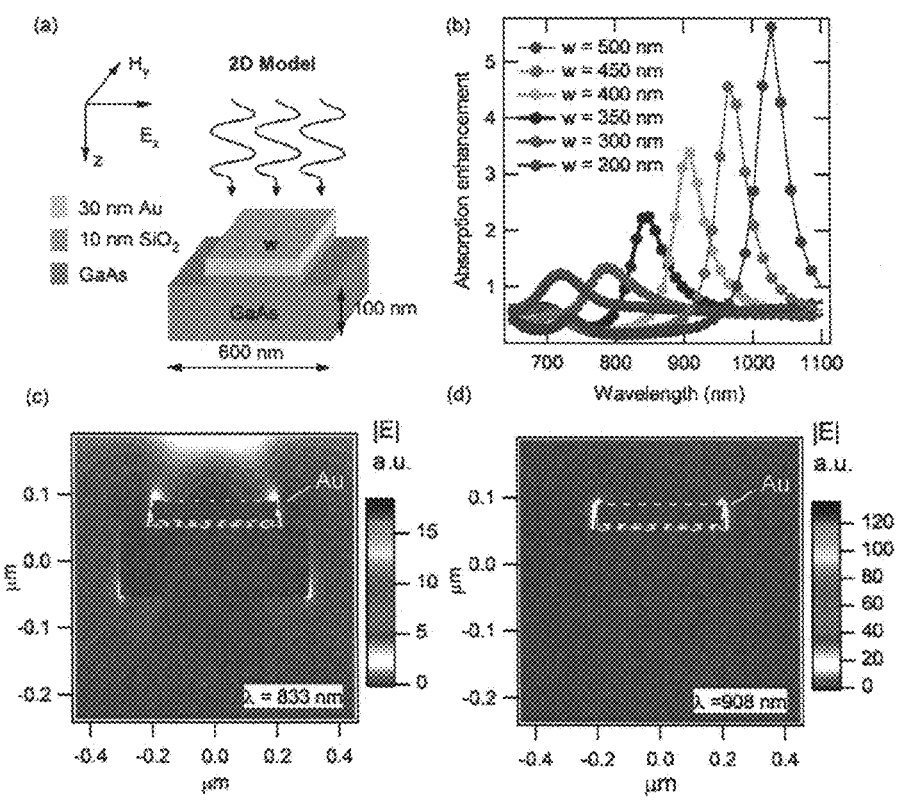
FIG. 2: shows (a) Geometry of the modeled device. (b) Response of the particle-semiconductor system compared to the response of photodetector without particle. The spectra show resonance peaks, with resonance wavelengths dependent on the width of the Au-structure. (c)-(d) Electrical field intensity for a device with a 400 nm width at (c) λ=833 nm and (d) λ=908 nm.

In FIG. 2 (a), the 2D modeled geometry of a semiconductor structure with particle attached to it is shown. FIG. 2 (b) shows the spectrum of absorption in the GaAs layer with a particle compared to the case of a GaAs structure without such particle. The spectra show clear resonance behavior; the mode-energy is strongly dependent on the width (w) of the gold structure. The resonance wavelength of the metal structures scales linear with the metal-semiconductor cavity size, offering wide-range tunability. The bandwidth of the resonance increases for higher resonance energy, indicating that the semiconductor quenches the Plasmon when the absorption in the semiconductor is high. In FIG. 2 (c) the electrical field intensity distribution of a structure with w=400 nm is plotted for an off-resonant excitation wavelength of 833 nm. In FIG. 2 (d) the distribution is shown for an excitation at resonance at 908 nm. In the latter case the electrical fields are strongly amplified. It is evident from FIGS. 2 (c) and 2 (d) that the largest electrical fields are developed across the $SiO_2$ layer which serves as a spacer layer for the charges in the gold structure and their respective image charges in the GaAs. The occurrence of 4 spots with high electric field intensity indicates that a multi-pole is excited. The Plasmon-enhanced electrical fields in the GaAs layer lead to enhanced light absorption. Similar calculations learn that the dipole-modes of the metal-dielectric cavity can be excited in the wavelength range 1250 nm-1800 nm for the same structures.

Figure 3:
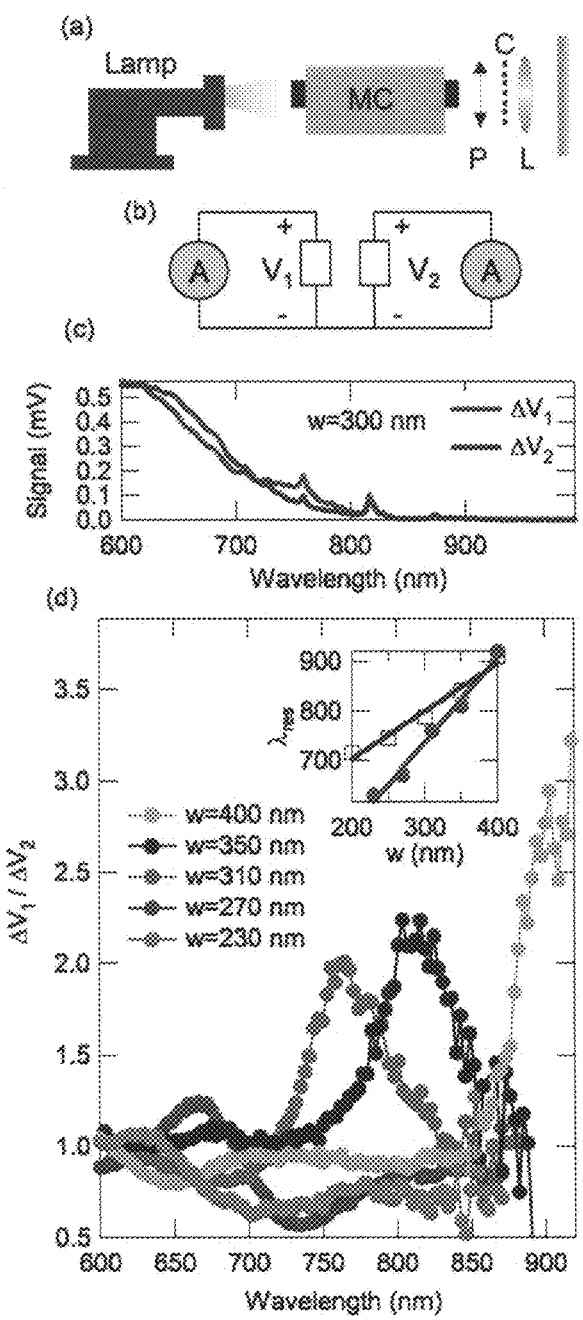
FIG. 3: shows (a) Sketch of the measurement setup: light from a Xenon lamp is spectrally decomposed with a monochromator, linearly polarized (P), modulated (Chopper C), and focused on the sample. (b) Electrical scheme: a constant current, 0.2 mA, is applied on the detectors with and without particle. The relative response ($\Delta V_1/\Delta V_2$) is recorded with a lock-in amplification technique. (c) Measured response for a detector with ($\Delta V_2$) and without particle ($\Delta V_1$), w=300 nm. In panel (d) the measured response for devices with w=230 nm, 270 nm, 310 nm, 350 nm, 400 nm are shown. In the inset the measured (●) and simulated (□) resonant colors ($\lambda_{res}$) as a function of w are plotted and compared.

The experimental setup for spectral analysis is described in FIG. 3 (a). Light from a 300 W Xe lamp is passed through a monochromator (MC) for wavelength selection and is subsequently linearly polarized (P), modulated with an optical chopper (C) and focused on the sample with a lens (L). The electrical configuration is outlined in FIG. 3 (b). A device with particle and a reference device without particle are measured simultaneously, a current of 0.2 mA is applied and the amplitude modulations (rms.) in electrical response, $\Delta V_1$ and $\Delta V_2$ respectively, are measured with a lock-in detector. All devices have a resistance of 3.5-4.5 k$\Omega$. FIG. 3 (c) shows the frequency response of the lock-in signal of the photodetector with particle and without particle. The spectra contain features from the lamp spectrum, the grating spectrum and the wavelength dependent absorption characteristics of the GaAs detector. The signal enhancement, $\Delta V_1/\Delta V_2$, for devices with w=230 nm, 270 nm, 310 nm, 350 nm, 400 nm are shown in FIG. 3 (d). All gold structures have a length of 5 micron, the width of the GaAs photodetector was 600 nm. The dimensions of the devices were evaluated with SEM, the thickness of the Au and $SiO_2$, 30 nm and 10 nm, were evaluated by means of Atomic Force Microscopy (AFM). The predicted response (FIG. 2 (b)) is reproduced; in the inset the calculated and measured resonance frequencies are plotted and compared. The strongly reduced absorption efficiency for GaAs at energies lower than the bandgap energy at room temperature, resulting in a strongly reduced signal for both detectors, restrains the upper limit of the measurement window to 920 nm. An excellent signal to noise ratio, however, can be reached at energies higher than the bandgap, with a large optical spot-size (>1 $mm^2$) and at limited optical input power, indicating the scalability of the technique towards smaller metal structures and indicating the possibility of studying arrays of devices.

Figure 4:
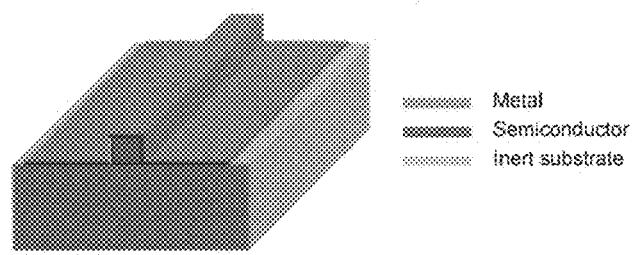
FIG. 4: shows an example implementation. Subwavelength corrugated semiconductor covered with metal film. Metal film serves to make the device biospecific, passivates the surface and screens unwanted influences of external charges.

As a further example, continuous metal films deposited on top of a nano-structured photodetector volume can be used. The structuring of the metal film induced by the photodetector gives rise to local optical modes that are responsible for efficient local transduction of optical energy into the photodetector. Furthermore, the continuous metal film effectively screens the photodetector from nearby charges that can distort the local electrical measurement and it can chemically passivate the entire structure. FIG. 4 illustrates the above described embodiment. This approach is particularly effective for very small widths of the semiconductor photodetector (<100 nm). For practical reasons it might be desirable to employ somewhat larger photodetector volumes (e.g. because the intrinsic sidewall roughness can cause additional depletion effects for small photodetectors). For larger widths, however, the excitation of the cavity resonance leading to enhanced absorption can be suppressed by the screening of the continuous metal film. In order to still effectively couple to the cavity resonance, additional topological nanofeatures can be introduced, such as grooves or indentations, leading to localized modes that evanescently couple to the interior cavity plasmon resonance.

Figure 5:
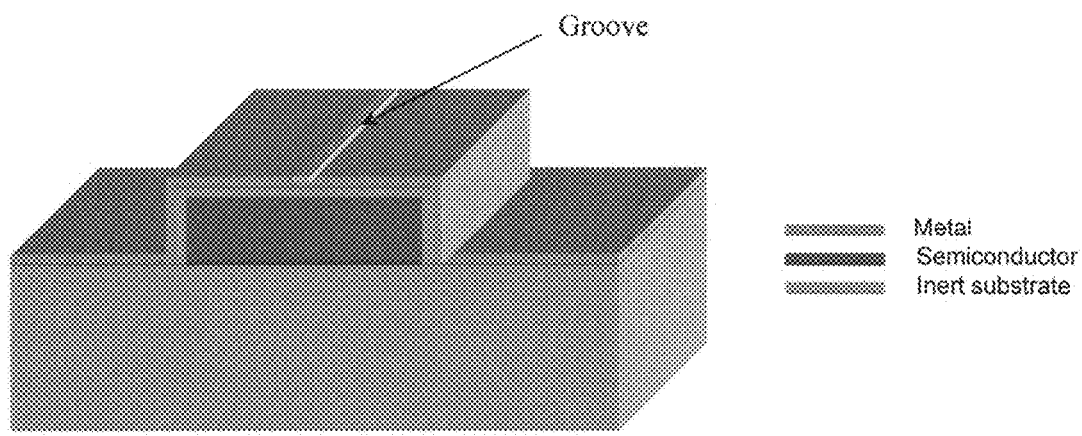
FIG. 5 shows an embodiment of the present invention in which a subwavelength corrugated semiconductor is covered with metal film. The metal film serves to make the device biospecific, passivates the surface and screens unwanted influences of external charges. A nanostructure window such as a groove in the metal film in the center couples the externally incident light to the cavity resonance of the photodetector.
Figure 6:
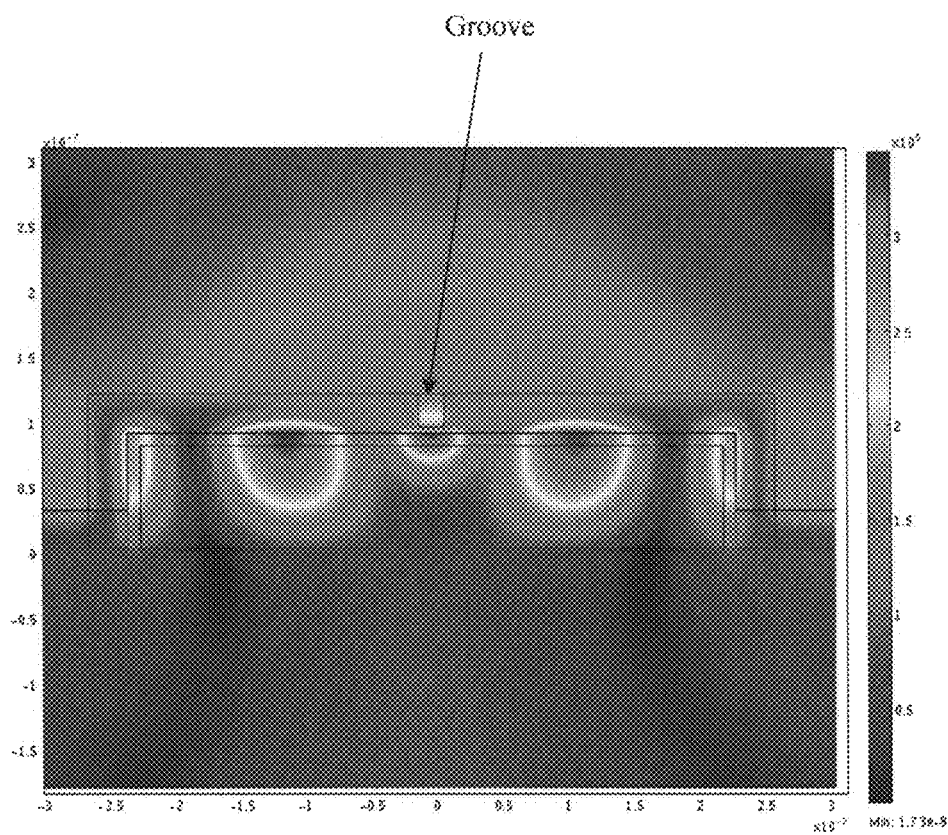
FIG. 6 shows a simulation of the electromagnetic field profile (the magnetic field in this case) at resonance conditions for a structure as depicted in FIG. 5. It is clear that the localized plasmon resonance of the groove couples to the cavity resonance at the metal/semiconductor interface.

FIGS. 5 and 6 show an example of such an implementation and the simulated electromagnetic field profile. FIG. 5 shows an embodiment of the present invention in which a subwavelength corrugated semiconductor is covered with a metal film. The metal film serves to make the device biospecific, passivates the surface and screens unwanted influences of external charges. A nanostructure providing a coupling window such as a groove is provided in the metal film in the center. The groove couples the externally incident light to the cavity resonance of the photodetector. The groove also provides sites for local optical modes that are responsible for efficient local transduction of optical energy into the photodetector, i.e. the coupling window also provides localized plasmon resonance.

FIG. 6 shows a simulation of the electromagnetic field profile (the magnetic field in this case) at resonance conditions for a structure as depicted in FIG. 5. It is clear that the localized plasmon resonance of the groove couples to the cavity resonance at the metal/semiconductor interface.

An advantage of such a localized excitation is the possibility to excite modes in the cavity that don't interfere strongly with the metal sidewalls, which can suffer from roughness. Furthermore, by e.g. tuning the size of the groove, the localized excitation can be engineered as to adapt the sensitivity to different types of analytes. In conclusion, a technique is presented for the local transduction of a Plasmon resonance in a single metal nanostructure or a metal film by means of an optical detector fabricated in the particle's near field. The response of the particle-photodetector system or the film-photodetector system can be simulated by means of a FDTD method and compared with experimental results. The dependence of the response on the width of the gold particle or gold film can be analyzed. Good agreement between experimental and modeling results can be obtained. The method and the device allow applications in biosensing and optical signal processing.

Alternative embodiments of the invention can be based on plasmonic antenna structures for the design of fast and low-noise optical sensors with enhanced response in the IR spectrum. The design method of the present invention can enable further scaling of structures and optimizing systems for maximized sensitivity. Lower bandgap semiconductors can be used as photo-active material to enlarge the spectrum measurable; this should allow to measure dipole resonances in the 1100 nm-1800 nm wavelength window. Furthermore, the use of biocompatible substrate materials is possible.

It is to be understood that although preferred embodiments, specific constructions and configurations, as well as materials, have been discussed herein for devices according to the present invention, various changes or modifications in form and detail may be made without departing from the scope of this invention as defined by the appended claims.

What is claimed is:

1. A method for determining the concentration of an analyte using a substrate comprising a conductive region and a recognition layer, the conductive region having a first surface operatively coupled with the recognition layer, the conductive region comprising at least one metal particle or structure having a near field and a semiconductor disposed in the near field of the at least one metal particle or structure, the semiconductor being part of a photodetector, the method comprising:
   contacting the substrate with the analyte to bind at least a portion of the analyte with the recognition layer;
   directing radiation to the conductive region and the recognition layer, the combination of the at least one metal particle or structure, the semiconductor and the analyte exhibiting plasmon effects when the radiation is directed to the conductive region and the recognition layer;
   electrically transducing the response of the said plasmonic excitation of the combination of the metal particle or structure, analyte and semiconductor, through light absorption in the semiconductor and subsequent change of the conductivity of said semiconductor, at least a part of a spectrum being related to said plasmon effect being absorbed in the semiconductor through scattering into the semiconductor and subsequent absorption or through evanescent coupling to the semiconductor; and
   determining the concentration of the analyte from at least part of the spectrum of said light absorption.

2. A method according to claim 1, wherein said photodetector and said metal particle or structure optimize the sensitivity of said absorption spectrum to binding of said analytes.

3. A method according to claim 1 wherein said photodetector is a free-standing structure, and wherein mechanical properties of the free-standing structure are measured to provide additional information on the analyte.

4. A method according to claim 1 wherein said photodetector is made from one or more light absorbing semiconductor materials forming a photosensitive diode, a photoconductor, or a structure displaying a photoelectric response.

5. A method according to claim 1, wherein said at least one metal particle forms a film covering or encapsulating partly or completely said photodetector and acting as an environmental protection layer for the photodetector.

6. A method according to claim 1 wherein said absorption spectrum is compared with a reference spectrum.

7. A method according to claim 6 wherein the metal film or structure encapsulating partly or completely said photodetector acts as an electronic shielding layer, screening the influence of environmental electronic charges on the electronic properties of the semiconductor.

8. A method according to claim 1 wherein the radiation is directed from free space or from a light or from a plasmon waveguide.

9. A method according to claim 1 wherein the analyte is bound to at least one nanoparticle, and wherein said nanoparticles contribute to the plasmon effect after binding of the analyte with the recognition layer.

10. A method according to claim 1 wherein a molecular resonance of the analyte changes said absorption spectrum.

11. A method according to claim 1 wherein said binding between analyte and recognition layer is a surface interaction between a gas analyte and a solid recognition layer.

12. A method according to claim 1 wherein one or more metal particles or structures are constructed local to one or more semiconductor volumes.

13. A method for determining the concentration of a plurality of analytes in parallel within a sample, the method comprising:
   substantially simultaneously performing the method according to claim 1 at a plurality of places on said substrate, each of said places having at least one metal particle and a specific recognition layer of one of said plurality of analytes with a plurality of photodetectors.

14. A method according to claim 13 wherein at each of said places, said photodetector and said metal particle transduce radiation to an electrical signal within said photodetector for the metal particle, photodetector and recognition layer combination at a specific place.

15. A method according to claim 13, wherein one or more metal particles or structures are constructed local to one or more semiconductor volumes.

16. A method according to claim 13 wherein mechanical properties of the freestanding structure are measured to provide additional information on the analyte.

17. A structure for determining the concentration of an analyte comprising:
   a substrate;
   a conductive region, said conductive region comprising at least one metal particle or structure;

a semiconductor region disposed in the near-field of the at least one metal particle or structure, the semiconductor region being part of a photodetector;

a recognition layer operatively coupled with a first surface of said the conductive region; and an analyte in contact with said recognition layer;

wherein the combination of the at least one metal particle or structure, the semiconductor and the analyte exhibits plasmon effects upon direction radiation at the conductive region and the recognition layer.

18. A structure according to claim 17 wherein said recognition layer is chosen such that it binds at least a portion of said analyte.

19. A structure according to claim 17, wherein said semiconductor is such that the response of the said plasmonic excitation of the combination of the metal particle or structure, analyte and semiconductor volume, is electrically transduced through light absorption in the semiconductor and subsequent change of the conductivity of said semiconductor.

20. A structure according to claim 19 wherein at least part of the spectrum related to said plasmon effect is absorbed in the semiconductor through scattering into the semiconductor and subsequent absorption or through evanescent coupling to the semiconductor.

21. A structure according to claim 19 wherein the concentration of the analyte is determined from at least part of the spectrum of said light absorption.

* * * * *